United States Patent [19]

Olmo et al.

[11] Plant 5,056

[45] May 31, 1983

[54] TABLE GRAPE

[75] Inventors: Harold P. Olmo; Albert T. Koyama, both of Davis, Calif.

[73] Assignee: Regents U.C., Berkeley, Calif.

[21] Appl. No.: 115,835

[22] Filed: Jan. 28, 1980

[51] Int. Cl.[3] ..... A01H 5/00

[52] U.S. Cl. ..... Plt./47

[58] Field of Search ..... Plt./47

*Primary Examiner*—James R. Feyrer

*Attorney, Agent, or Firm*—Townsend and Townsend

[57] ABSTRACT

A new and distinct variety of grapevine capable of producing late harvest red table grapes similar to the Emperor variety but which is superior to Emperor in its heavier and more regular cropping and in its greater uniformity of color, largeness of berry size and better palatability.

3 Drawing Figures

DESCRIPTION

This invention relates to a new and distinct variety of grapevine of the *vinifera* species to be utilized as a late harvest table grape similar to the commercial variety Emperor, to which it is superior in heavier and more regular cropping, more uniform and earlier red coloring, larger berry size and improved palatability.

Figure 1:
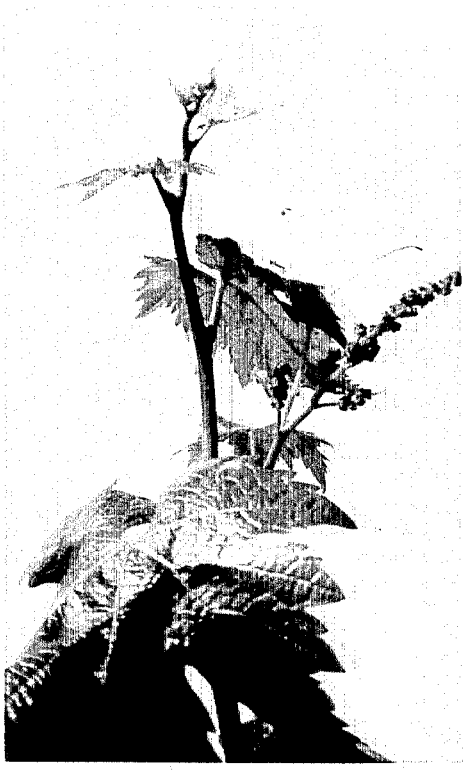
FIG. 1 is a drawing of a typical shoot tip of a plant of the new variety.
Figure 3:
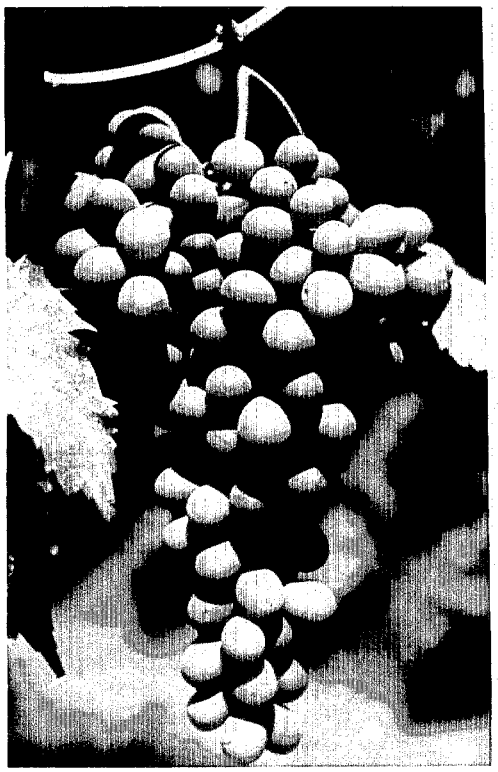
FIG. 3 is a drawing of a typical cluster of the new variety.
Figure 2:
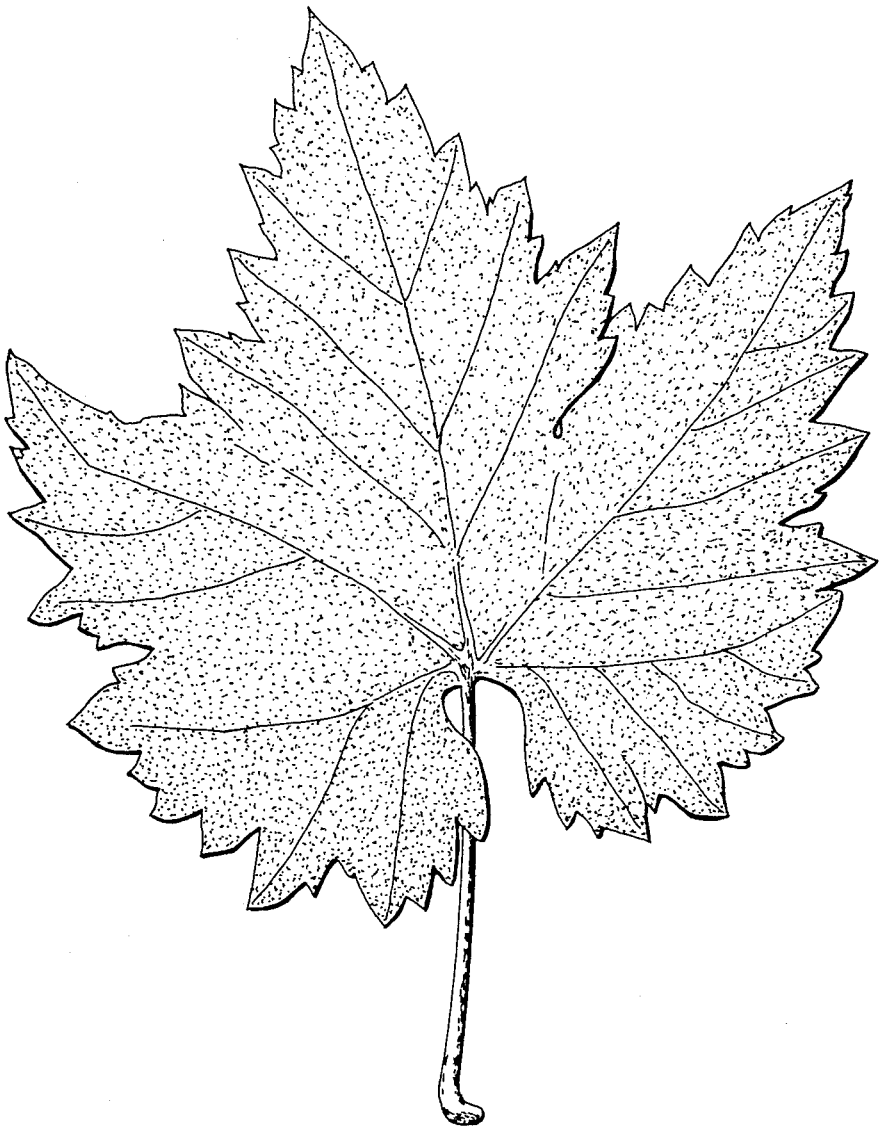
FIG. 2 is a drawing of a typical leaf of a plant of the new variety shown reduced from actual size.

The new variety is the result of the following heritage.

c15-47 [ S44-35c × 9-117D ]
- S44-35c [ L12-80 × NOCERA ]
  - L12-80 [ EMPEROR × G24-87 [HUNISA, O.P.
  - NOCERA
- 9-117D [ L12-80 × 17-11 ]
  - L12-80 [ EMPEROR × G24-87 [HUNISA, O.P.
  - 17-11 [ EMPEROR × I.P.75 ]

The cross yielding of the new variety, that is S44-35c×9-117D, was made at Davis, Calif., in 1962, the seedling vine c15-47 was observed to be promising in its first year of bearing, 1966, from a progeny of 183 seedlings planted in the vine in 1963. The variety was then asexually reproduced from cuttings taken from the original seedling selection in the spring of 1964 at the Kearney Horticultural Field Station, Parlier, Calif. The variety has been tested at the Kearney Horticultural Field Station and was found to maintain the same essential characteristics.

The colors referred to in the following description under the heading Plant Characteristics are subject to substantial variation and are not considered distinctive or diagnostic features of the plant of this invention.

PLANT CHARACTERISTICS

Vine: Vigorous, trunk of large diameter, producing many straight and vigorous canes, good cover of foliage canopy, very productive when spur (two buds each) pruned, blossoming and budding out several days to one week before Emperor. Fruit fully colored by the middle of August in the Fresno, Calif., region.

Shoot Tip (10"–12"): Incurved, arachnoid hairy, leafy, golden sheen, first flat leaf with three lobes, very elongated terminal teeth, narrow and sharp.

Shoot: Strongly incurved at summit; tendrils very large, slender, with miniature leaf at first bifurcation, lateral shoots remain short but develop early; inflorescence usually one per shoot, borne at node six, long, slender, laterals widely spaced on rachis, apex often bifurcate, at time of full blossom calyptras dry and shed, self-pollinates before calyptras shed, stamens with weak and fragile filaments.

Cane: Straight and long, thinner and weaker than Emperor, light brown with darker brown on exposed portions, and at nodes, prominent striations, round in x-section, buds small, pointed, tightly sealed.

Leaf: Blade 19.8×18.3 cm., distinctly three-lobed, glabrous above and below, with lateral lobes very acute and extended beyond leaf margin, superior sinuses shallow, very narrow, closed by overlapping lobes, inferior sinuses reduced to small notches; petiolar sinus open wide, deep, lyre-shaped; teeth very large, equilateral, in two series, secondary almost as large as apical ones; petiole slender 11.2 cm. long, 3.1 mm. wide.

Cluster: Long conical, large to very large, 1376 gm., from attachment of peduncle to tendril 1.7 cm., from tendril to first rachis branch 4.1 cm., fruiting portion 26.7 cm., well-filled, peduncle woody at base only.

Berry: As the berries reach full coloration, the skin color is 'strong red' 5R 4/12 (color notations are made from Nickerson Color Fan, 1957, Munsell Color Company, Baltimore 2, Md. and at a later stage of maturity are 'deep purplish red' 7.5 R.P 3/9. Coloring begins earlier and is completed by the time the first color is appearing in Emperor. The new variety is less dependent on light for color development and does not require the heavy defoliation and cane positioning used in Emperor culture in order to admit light.

The seeds are large, 5×9 mm, the body color 'moderate yellowish brown,' 10 YR 4/4, with lighter colored ventral folds 'dark orange yellow' 10 YR 5/6. The ridge and beak are straight, thus the seed lies almost flat on the ventral surface; the chalaza is small, only slightly depressed, with a smooth cavity that is elongated as it merges into the trough of the raphe. The seeds are hard but not astringent when eaten. The seed frequencies of the 10 largest berries per cluster are 13 percent with 1 seed per berry, 42 percent with 2 seeds, 40 percent with 3 seeds and 5 percent with 4 seeds. Weight of 100 seeds air-dried is 4.7 gm. The berry flesh does not adhere to the seeds and they are easily extracted.

The skin is thin and tender, but resistant to cracking. The pedicels are 8–10 mm in length, slender and with a small and not widely flanged torus for such large berries, with few and small lenticels. The brush is 4–5 mm in length, firmly imbedded and has red vascular traces. Adherence of the berry is not equal to Emperor, but test shipments indicated very good shipping and cold storage qualities without shattering. The berry skin is covered with a moderate waxy bloom.

The palatability of both fresh and cold-stored fruit appears superior to Emperor because of better eye appeal — larger and brighter colored berries — as well as a thinner skin, crisper flesh, higher sugar content and better acid balance. In mid August, at Fresno, Calif., the new variety tests from 16 degrees to 18 degrees Brix and total acidity from 0.6 to 0.8 gm (as tartari acid per 100 cc of juice). No distinctive flavor is present, hence "neutral."

Disease and Insect Resistance: The vine has exhibited no particular or unusual instance of disease or insect tolerance of those pests ordinarily found in Californian vineyards, reacting much the same as other *vinifera* cultivars.

We claim:

1. The new and distinct variety of table grape herein described and illustrated and identified by the characteristics enumerated above.

* * * * *